(12) United States Patent
Chang et al.

(10) Patent No.: US 8,481,092 B2
(45) Date of Patent: Jul. 9, 2013

(54) ANTIMICROBIAL SUTURE FOR MEDICAL USE WITH GRAPEFRUIT EXTRACT, AND MANUFACTURING METHOD THEREOF

(75) Inventors: Jeong Ho Chang, Gwangmyeong-si (KR); Hye Sun Lee, Seoul (KR); Jin Hyung Lee, Hwaseong-si (KR)

(73) Assignee: Korea Institute of Ceramic Engineering and Technology, Seoul (KR)

( * ) Notice: Subject to any disclaimer, the term of this patent is extended or adjusted under 35 U.S.C. 154(b) by 178 days.

(21) Appl. No.: 12/914,352

(22) Filed: Oct. 28, 2010

(65) Prior Publication Data

US 2011/0135761 A1 Jun. 9, 2011

(30) Foreign Application Priority Data

Dec. 9, 2009 (KR) ........................ 10-2009-0121725

(51) Int. Cl.
*A61K 36/752* (2006.01)
*A61K 36/00* (2006.01)

(52) U.S. Cl.
USPC .......................................... 424/736; 424/776

(58) Field of Classification Search
None
See application file for complete search history.

(56) References Cited

U.S. PATENT DOCUMENTS

2007/0212387 A1  9/2007  Patravale et al.
2007/0212393 A1* 9/2007  Patravale et al. .............. 424/423

FOREIGN PATENT DOCUMENTS

| CA | 786758 A | * | 7/1964 |
| JP | 2004250804 A | * | 9/2004 |
| KR | 10-2003-0037094 A | | 5/2003 |

OTHER PUBLICATIONS

KIPO Office Action for Korean Patent Application No. 10-2009-0121725 which corresponds to U.S. Appl. No. 12/914,352.

* cited by examiner

*Primary Examiner* — Chris R Tate
(74) *Attorney, Agent, or Firm* — LRK Patent Law Firm (57) ABSTRACT

A method of manufacturing a medical antimicrobial suture having a grapefruit extract which is a grapefruit seed extract including naringin, ascorbic acid or citral is provided. The method includes preparing grapefruit extract solution with a concentration of 500 to 2000 ppm by mixing the grapefruit extract with methanol solvent; and impregnating a biodegradable monofilament suture with the grapefruit extract solution for more than 360 minutes. The grapefruit extract is continuously released in a body for 70 hours after the antimicrobial suture is inserted into the body.

1 Claim, 9 Drawing Sheets

ANTIMICROBIAL SUTURE FOR MEDICAL USE WITH GRAPEFRUIT EXTRACT, AND MANUFACTURING METHOD THEREOF

CROSS-REFERENCE TO RELATED APPLICATIONS

This application claims the priority of Korean Patent Application No. 2009-0121725, filed on Dec. 9, 2009, in the Korean Intellectual Property Office, the disclosure of which is incorporated herein by reference.

BACKGROUND OF THE INVENTION

1. Field of the Invention

The present invention relates to the enhancement of antimicrobial activity of a biodegradable or non-biodegradable suture used during surgery, and more particularly, to the enhancement of antimicrobial activity of a suture by functional materials included in a grapefruit extract having an antimicrobial effect by immersing the suture in a solution in which the grapefruit extract is dispersed.

2. Description of the Related Art

A suture is an important medical suturing material used such that the open parts of a surgical site are drawn together and located in position until the wound is healed up. Conditions required for the suture as a medical material include high biocompatibility, chemical stability, flexibility, durability, heat resistance, moldability, and processability, as well as low production cost.

Examples of such sutures include absorbable sutures and non-absorbable sutures. The absorbable sutures include natural sutures such as catgut and collagen, synthetic sutures such as PGA and PLA, and the non-absorbable sutures include polyester, nylon, etc.

The history of surgical sutures starts with a record that the Egyptians used tendons or strings as sutures in 3000 BC, and since then, through the Roman Era and the Middle Ages, a bioabsorbable suture was developed from goatskin and deerskin in 1806 for the first time by the University of Pennsylvania School of Medicine. Since then, synthetic sutures were developed and used about 50 years ago, and synthetic bioabsorbable sutures have recently been produced in various forms such as a hard clip, etc.

Meanwhile, catgut made of extracts from organs of animals such as cattle, sheep, etc. was widely used until the 1970s, but its use has gradually decreased due to low strength, which causes poor productivity, and due to tissue response, which causes side effects. Catgut originated from the use of intestines of cats and, since the 1970s, surgical sutures made from synthetic fibers, in which ester groups of polymer are hydrolyzed by body fluid in tissues and absorbed by themselves, have been steadily developed.

The synthetic sutures may be broadly classified into a polyglycolic acid (PGA) suture made by twisting several strands of thread and a polydioxanone (PDO) suture made of a single strand of thread. The PDO suture consists of a single strand of thread and thus has low flexibility and elasticity, but its surface is smooth and the risk of bacterial infection is low due to no space between threads. On the contrary, the PGA suture is made by twisting several strands of thread and thus has high flexibility and elasticity, but its surface is rough and the risk of bacterial infection is high due to the space created between the threads.

A poly(glycolide-co-L-lactide) (PGLA) suture developed to overcome the drawbacks of the above-mentioned two type of sutures is a copolymer, which is polymerized using glycolide and lactide as raw materials and thus has good flexibility and elasticity. Moreover, the roughness of its surface can be reduced by improving coating efficiency using calcium stearate as a coating material.

Moreover, the biodegradation period of the PGA and PLA homopolymers depends on the molecular weight, but is generally more than one year. However, the PGLA as a copolymer thereof is biodegraded over several weeks to months depending on the molecular weight.

Conditions required for the above various sutures are to have suitable tension and elasticity, to cause no reaction in the tissues, and to provide an environment where germs, bacteria, or viruses cannot grow.

Furthermore, the suture should not cause allergic and hypersensitive reactions or have no carcinogenicity, should be convenient to use, should prevent a knot or string from being easily untied or cut, should be easily cut after making the knot, and should prevent its form or composition from changing during autoclave sterilization. Meanwhile, since the reformation of scar is slowly made, the suture should have a certain amount of strength that is maintained for the period required for the induction of tissue.

As such, the biodegradable suture should be convenient to use and should reduce the occurrence of infection during surgery.

In order to solve the problem of the occurrence of secondary infections due to the suture, materials having an antimicrobial effect such as nano-silver particles have been conventionally used to impart antimicrobial activity to the sutures. However, when these nanoparticle materials are introduced into the body, they remain in the body for a long time, which is problematic.

Meanwhile, naringin as one of the components of the grapefruit extract is a type of flavonoid known as vitamin P having an antimicrobial effect, mainly present in the seed and peel of a ripe grapefruit, and tastes bitter. Its molecular formula is $C_{27}H_{32}O_{14}2H_2O$ and its chemical structure may be represented by the following chemical formula 1:

[Chemical Formula 1]

The main functions of the naringin are as follows. First, the naringin has a bacteriostatic effect to inhibit the growth of microorganisms in food and an antimicrobial effect to sterilize microorganisms. Moreover, the naringin has an antioxidative action and is a strong antioxidant that has a greater effect than fat-soluble tocopherol in food. In particular, the naringin is water-soluble and thus has a wide range of uses and is non-toxic even after excessive intake.

The principle of the antioxidative action of the naringin may be simply represented by the following chemical formula 2:

[Chemical Formula 2]

Moreover, the naringin has a metal chelating action to interfere with the enzymatic reaction in a cell membrane, thus inhibiting the growth of bacteria. In addition, the naringin has the potentiating effect of ascorbic acid to improve the stability of ascorbic acid in food. Furthermore, the naringin has the ability to inhibit the growth of malignant cells and an anticancer effect to restore cells damaged by carcinogens.

The present inventors have developed a suture and a manufacturing method thereof, which has an antimicrobial activity and prevents nanoparticles from remaining in the body by applying a grapefruit extract containing naringin with these various functions to the suture.

SUMMARY OF THE INVENTION

The present invention has been made in an effort to solve the above-described problems associated with prior art, and an object of the present invention is to provide a suture and a manufacturing method thereof, which can prevent infections that may occur during surgery and prevent unsanitary conditions that may be encountered in a suture thread by applying a grapefruit extract having an antimicrobial effect to the suture, thus solving the problems of existing sutures.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

To achieve the above-described objects, the present invention employs a technique of immersing a suture in a solution containing a grapefruit extract to enhance antimicrobial activity.

Here, the grapefruit extract may be extracted from a grapefruit seed and may preferably comprise naringin, ascorbic acid, or citral.

Moreover, the suture may be made of a biodegradable component, and the biodegradable component may be selected from the group consisting of polyglycolic acid (PGA), polylactic acid (PLA), poly(lactide-co-L-lactide) (PLLA), poly(glycolide-co-L-lactide) (PGLA), polyglycolide (PG), polylactide (PL), and a mixture thereof.

Furthermore, the suture may be made of a non-absorbable component, and the non-absorbable component may be selected from the group consisting of polyester, nylon, polyacrylonitrile (PAN), and a mixture thereof.

In addition, the suture may preferably have a monofilament form for uniform distribution of the grapefruit extract and may further comprise calcium stearate as a coating material.

Meanwhile, to achieve the above-described objects, the present invention provides a method of manufacturing an antimicrobial suture for medical use, comprising i) preparing a suture, and ii) immersing the prepared suture in a grapefruit extract solution.

Here, the grapefruit extract solution may use a methanol solvent, and the concentration of the grapefruit extract solution may preferably be 500 to 2,000 ppm.

Moreover, the suture may preferably be immersed in the grapefruit extract solution for more than 150 minutes, but the test was performed at 360 minutes when the suture is sufficiently immersed in an optimum concentration.

The antimicrobial suture may prevent the pathogen infection by the antimicrobial function of the grapefruit extract. That is, the antimicrobial suture of the present invention may prevent fungi from being generated on the surface of the suture, which is a main cause of a secondary infection during surgery, and may stably maintain the strength and tension of the suture.

Hereinafter, an antimicrobial suture for medical use containing a grapefruit extract and a manufacturing method thereof will be described in detail with reference to the accompanying drawings.

The antimicrobial suture for medical use of the present invention contains a grapefruit extract.

Here, the suture may be made of a biodegradable component, a non-absorbable component, or a mixture thereof, the biodegradable component may be selected from the group consisting of polyglycolic acid (PGA), polylactic acid (PLA), poly(lactide-co-L-lactide) (PLLA), poly(glycolide-co-L-lactide) (PGLA), polyglycolide (PG), polylactide (PL), and a mixture thereof, and the non-absorbable component may be selected from the group consisting of polyester, nylon, polyacrylonitrile (PAN), and a mixture thereof.

Moreover, the grapefruit may be extracted from a grapefruit seed and may preferably comprise naringin, ascorbic acid, or citral.

In the following Examples, DF-100, a commercially available product, was used as the grapefruit extract. The biodegradable suture tends to be degraded and absorbed in vivo, and thus, when it is exposed to water for a long time, its strength is reduced, resulting in degradation of the biodegradable suture. Thus, it is preferable to minimize the reaction with water using methanol having a high evaporation rate as a solvent.

Preferably, the suture may have a monofilament form and may further comprise calcium stearate as a coating material.

The monofilament can prevent the proliferation of bacteria between threads, increase the antimicrobial activity due to uniform distribution of the grapefruit extract, and reduce the occurrence of infection associated with surgery. Moreover, a coating material such as calcium stearate may be used to smooth the rough surface of the suture and fill the space where bacteria may be parasitic.

Meanwhile, the method of manufacturing the antimicrobial suture for medical use may comprise i) preparing a suture, and ii) immersing the prepared suture in a grapefruit extract solution.

Figure 1:
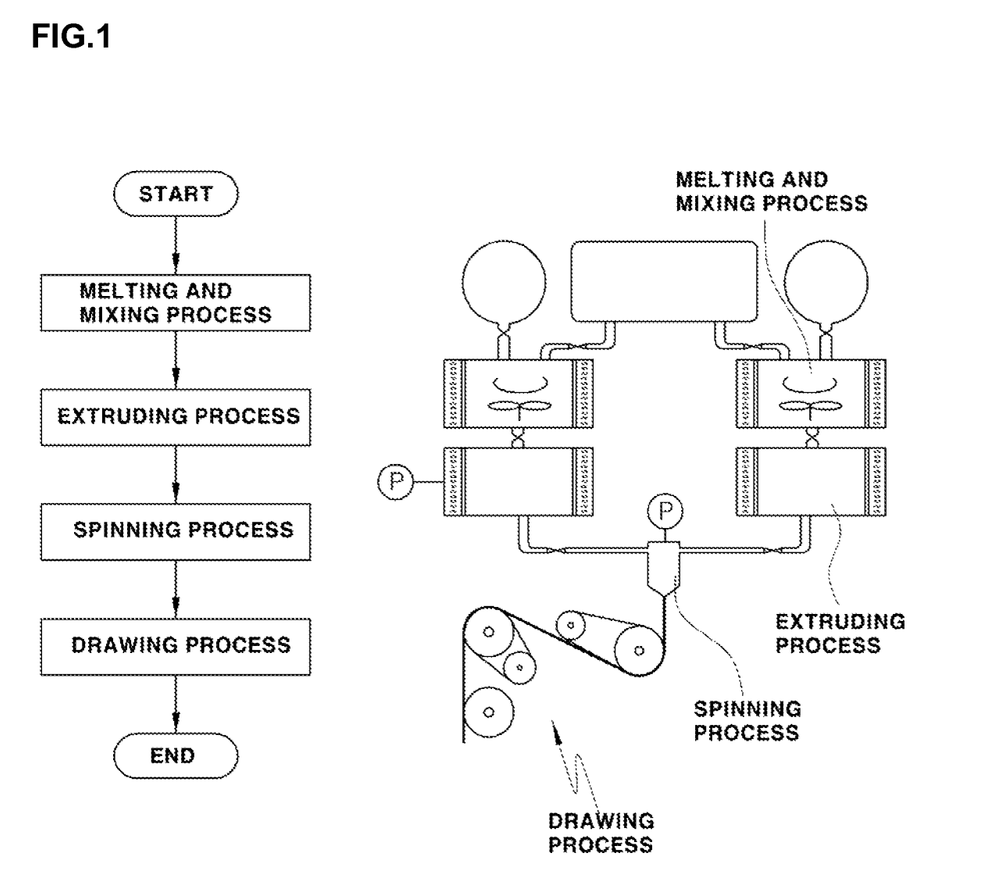
FIG. 1 is a diagram that represents the coating process of the suture thread.

FIG. 1 is a schematic diagram showing a process of coating a suture thread in accordance with an embodiment of the present invention, and the following chemical formula 3 represents the reactions associated with the manufacturing of a biodegradable monofilament suture that provides an easy procedure.

Figure 2:
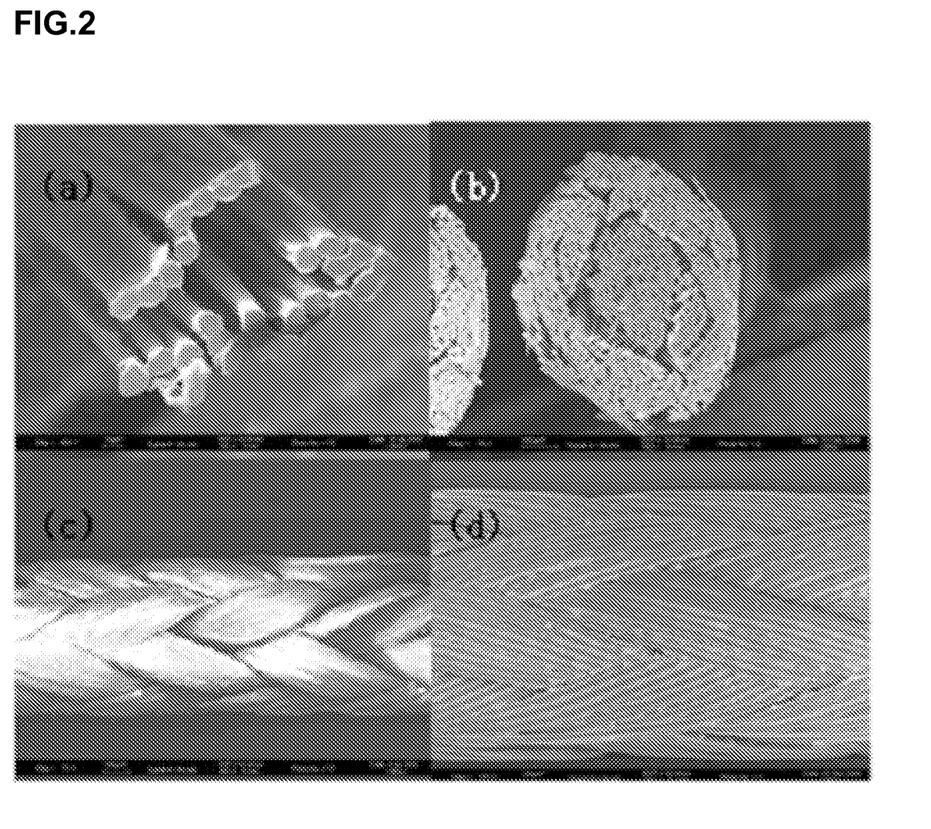
FIG. 2 is a FE-SEM analysis photograph of the suture thread according to one example of the present invention.

FIG. 2 shows FE-SEM images of sutures in accordance with an embodiment of the present invention. First, selected polymers were subjected to spinning in various composition ratios, and an optimum polymerization composition ratio was selected by comparing the physical properties for each of the polymerization composition ratios. Then, monofilaments having excellent handling properties and knot stability were prepared from selected compositions using a monofilament spinning machine under various spinning conditions.

Then, optimum conjugated monofilaments were prepared from the monofilaments using a composite spinning machine based on the test for each polymer composition.

Figure 3:
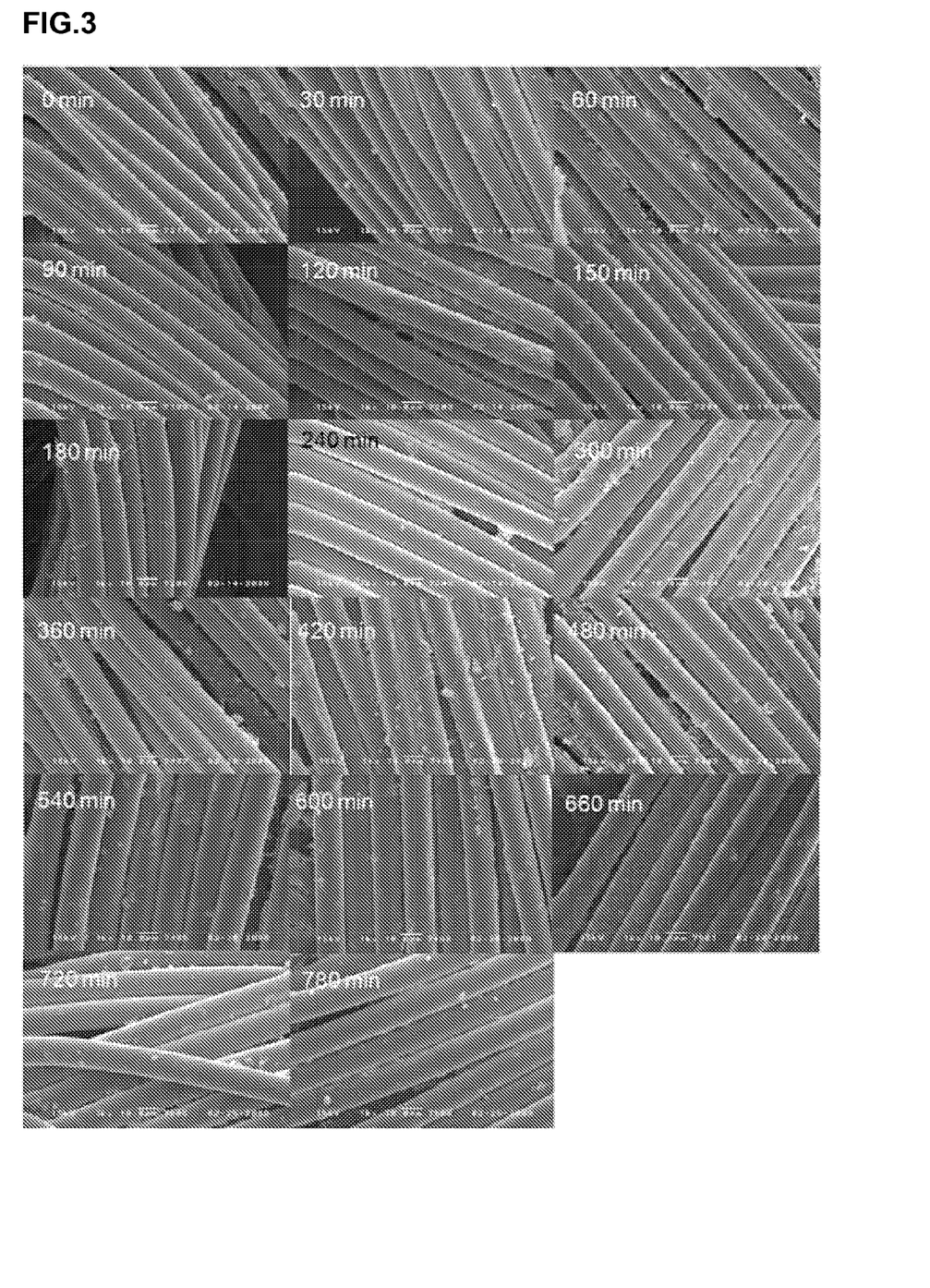
FIG. 3 is a SEM analysis photograph according to the time of the suture being contained in the grapefruit seed extract solution.

FIG. 3 shows SEM images taken over time after 1 g of each of the sutures prepared in the above manner was placed in a 30 mL solution of 100 ppm grapefruit extract and immersed in units of 30 minutes until the grapefruit extract was no longer absorbed into the suture.

As can be seen from the figure, there is almost no change in the thickness of the sutures due to the grapefruit extract contained in the sutures, and thus it is possible to minimize the inconvenience in use.

Next, Examples of the antimicrobial suture for medical use prepared according to the present invention will be described in detail. However, the following Examples are provided for a better understanding of the present invention, and the scope of the present invention is not limited to the following Examples.

Example 1

Preparation of PGLA (poly(glycolide-co-L-lactide))

Sutures used in the following Examples were prepared in general by four processes. First, poly-glycolide and lactide were melted into a gel state and then mixed with a pigment. At this time, the melting and mixing process was performed by placing the molten material and the pigment in a melting and mixing tank, which is separately provided, such that the melted material and the pigment could be easily mixed.

Then, an extrusion process in which the molten material was pressed in a pressure chamber and extruded by alternately closing and opening valves provided in the pressure chamber, a spinning process in which the extruded material from the pressure chamber was passed through a spinning nozzle to be extruded in the form of a thread, and a stretching process in which the spinning thread was stretched by a stretching machine to increase tensile strength and elasticity were performed sequentially.

Figure 9:
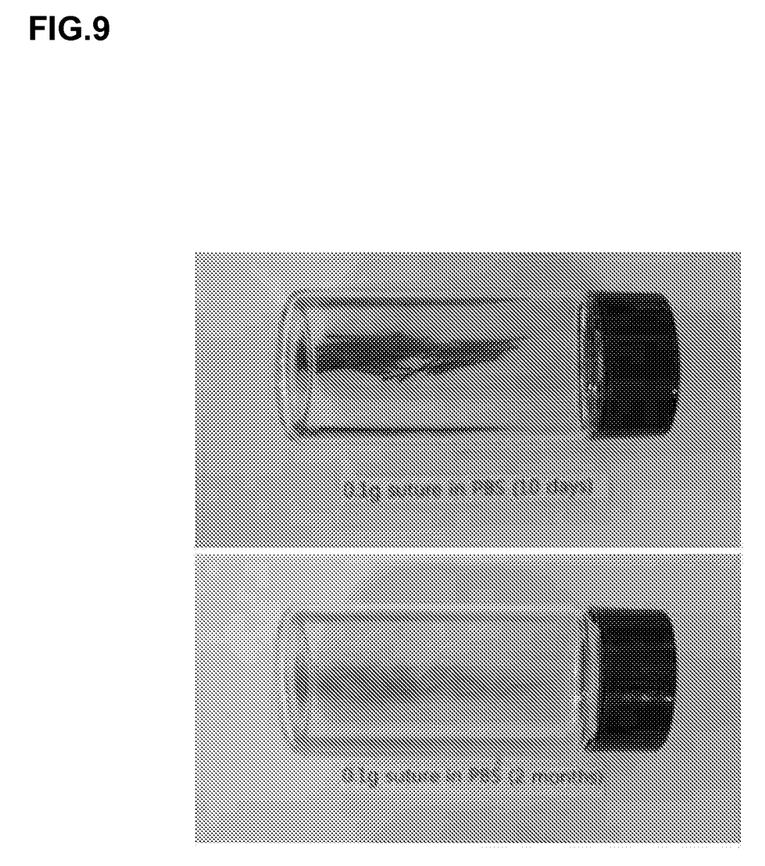
FIG. 9 is a photograph that represents the degradation result of the suture that contains the grapefruit extract according to one example of the present invention.

FIG. 9 shows images illustrating the degradation of 0.1 g of each of PGLA sutures in a PBS solution for 10 days and 2 months, respectively, from which it can be seen that the degradation of the sutures occurs very quickly. The higher the degradation rate, the higher the biodegradation rate, which results in a reduction in secondary infections.

Example 2

Preparation of Grapefruit Extract

Grapefruit extracts containing naringin in concentrations of 100 ppm to 1,000 ppm were prepared and tested. Methanol having a high evaporation rate was used as a solvent to prevent the sutures from being degraded by water when the sutures were immersed in the grapefruit extracts.

Figure 4:
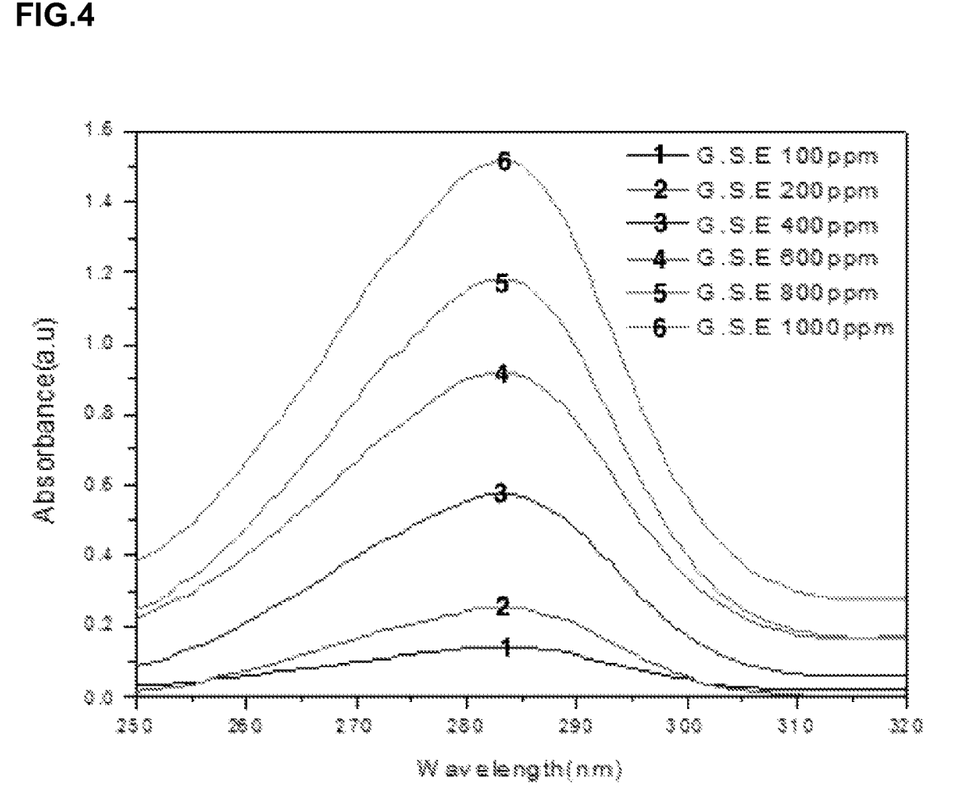
FIG. 4 is a UV-Vis analysis spectrum of the grapefruit seed extract according to one example of the present invention.

FIG. 4 shows the results of UV-VIS analysis of the extracts measured at a wavelength of 283 nm using JASCO V-550 UV-Vis spectrophotometer (wavelength range: 200 to 900 nm; bandwidth selectable: 0.5 nm; scanning speed: 400 nm/min; data pitch: 1 nm). It can be seen from the figure that the inherent wavelength of naringin is 283 nm.

Example 3

Immersion of Sutures in Grapefruit Extract Solution 1 g of each of the sutures prepared in Example 1 and 30 mL of each of the grapefruit extracts in a concentration of 1,000 ppm prepared in Example 2 were placed in a 30 mL vial and immersed for 0 minute, 30 minutes, 60 minutes, 90 minutes, 120 minutes, 150 minutes, 180 minutes, 240 minutes, 360 minutes, 420 minutes, 480 minutes, 540 minutes, 600 minutes, 660 minutes, and 720 minutes and, the resulting sutures were taken out and vacuum-dried.

Figure 5:
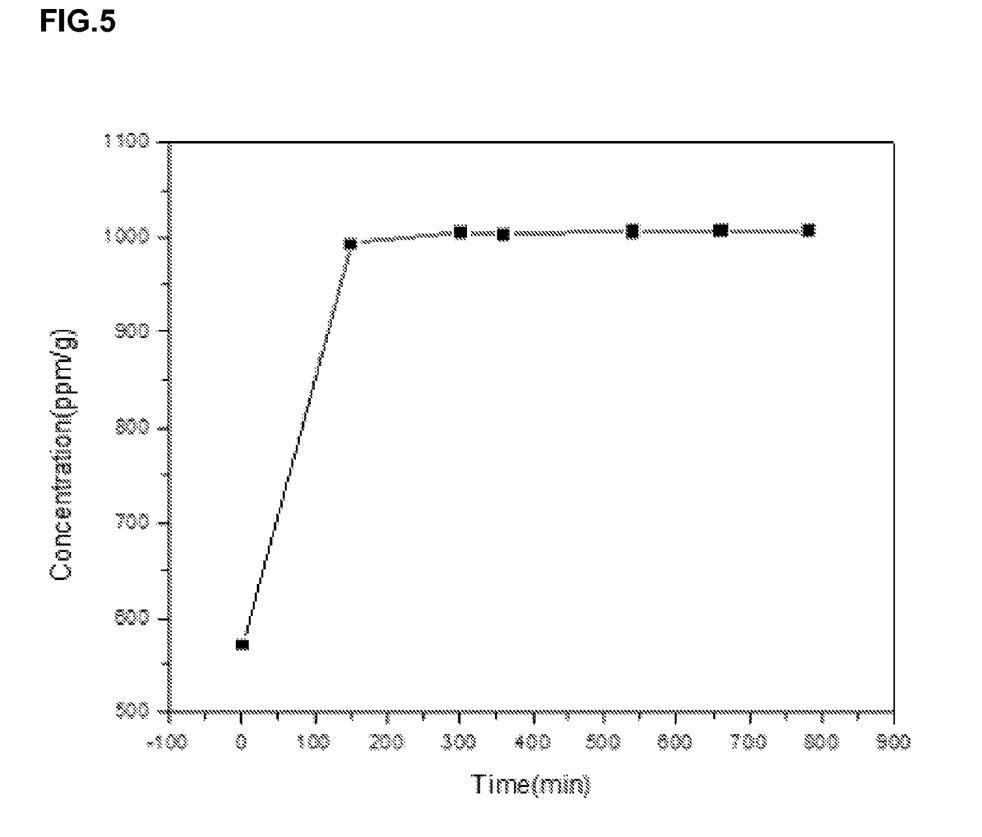
FIG. 5 is a graph that measures the amount of the grapefruit extract being contained in the suture according to the time.

In order to determine the absorption of the grapefruit extract into the suture, UV-VIS analysis was carried out on the remaining solution at a wavelength of 283 nm corresponding to the wavelength of the naringin, and the amounts of grapefruit extracts contained in the sutures according to the immersion time are shown in the graph of FIG. 5.

It can be seen from the results that the amount of naringin contained in the suture immersed for 30 minutes is the greatest and no longer increases after the immersion time of 150 minutes. Thus, it can be seen that the minimum immersion time is 150 minutes and the appropriate amount of naringin appears after more than 150 minutes. Hence, the test was performed at 360 minutes.

Example 4

Measurements of Drug Release

A test was performed to determine the in vivo drug release of the suture containing naringin for 360 minutes and prepared in Example 3.

0.01 M of PBS (0.01M of Monobasic monohydrate: 1.1832 g, dibasic ACS reagent: 8.1572 g using phosphate buffer calculator) was prepared as a solvent for the release test, and the pH was adjusted to 7.4.

Figure 6:
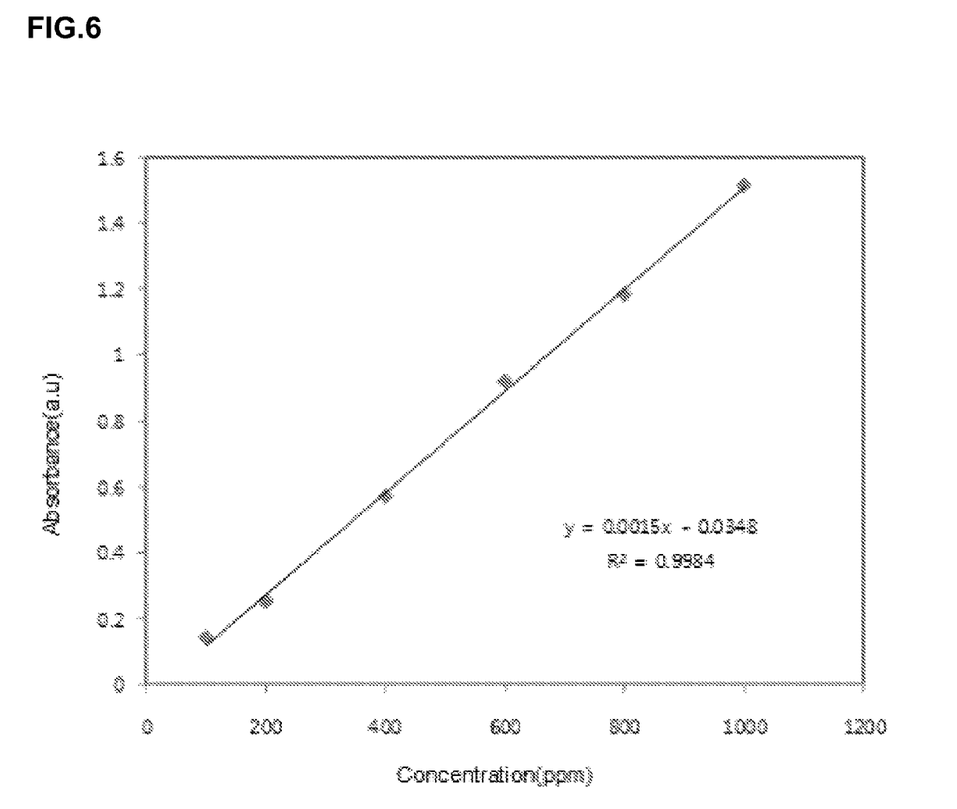
FIG. 6 is a standard curve graph for the grapefruit extract solution.

The test was performed with the grapefruit extracts in concentrations to make the standard curve shown in FIG. 6. The standard curve for the functional materials was obtained by measuring the absorbance using JASCO V-550 UV-Vis spectrometer (wavelength range: 200 to 900 nm; bandwidth selectable: 0.5 nm; scanning speed: 400 nm/min; data pitch: 1 nm). The standard curve equation shown in FIG. 6 is as follows. In the equation, x represents the concentration of the functional material, and y represents the absorbance.

$$y=0.0015x-0.0348$$

1 g of each of the sutures was immersed in a 30 mL solution of 1.000 ppm grapefruit seed extract, while stirring for 24 hours, and then filtered. The filtered sutures were dried, and then 1 g of each of the dried sutures was placed in a shaker and 5 mL of a 0.01 M PBS solution was added thereto. Then, 5 mL of each sample was extracted from the shaker for 2 hours, and then 5 mL of PBS solution was added again to the shaker. At this time, the temperature was maintained at 36.5° C. such that the test was performed under conditions similar to the temperature of the human body.

Figure 7:
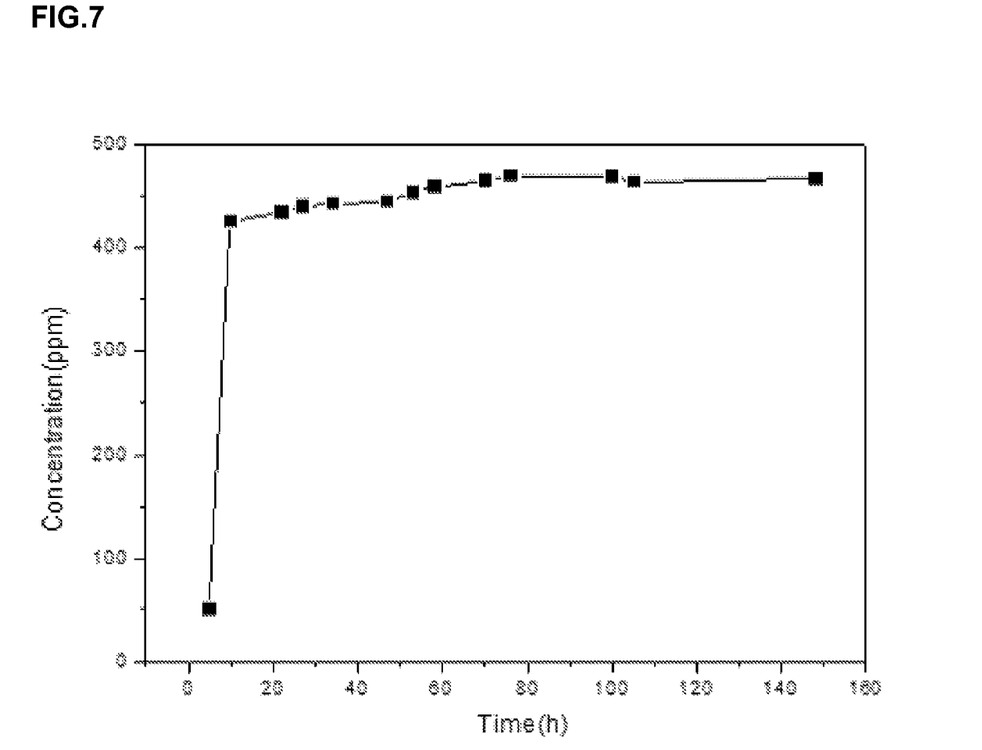
FIG. 7 is a graph that represents the cumulative value of ppm concentration according to the time and measures the release of the grapefruit extract material of the suture that contains the grapefruit seed extract.

FIG. 7 shows the results of the test, including the release profile of the grapefruit seed extract, from which the amount of grapefruit seed extract released in vivo over time can be seen.

As a result of observing the drug release of the sutures each containing the grapefruit seed extract according to the present invention for 0 to 150 hours, it was found that the drug release was completed after about 70 hours in substantially the same environment as the body. From this, it can be expected that the antimicrobial activity of the suture inserted into the body is maintained for about two to three days, from which it can be concluded that it is possible to reduce the risk of infection due to the presence of bacteria in the suture.

Example 5

Antimicrobial Activity

The antimicrobial activity of each of the sutures containing the grapefruit seed extract of Example 3 was tested in the following manner. That is, each suture containing the grapefruit seed extract was placed in a microbial culture medium at the early logarithmic phase. Then, when a culture medium that reacted with a suture containing no grapefruit seed extract as a control group reached the late logarithmic phase, 200 µl of cell culture medium was cultured at 30° C. for 24 hours, and the number of colonies formed by a strain was measured and compared. The used strain was *Staphylococcus aureus*.

Figure 8:
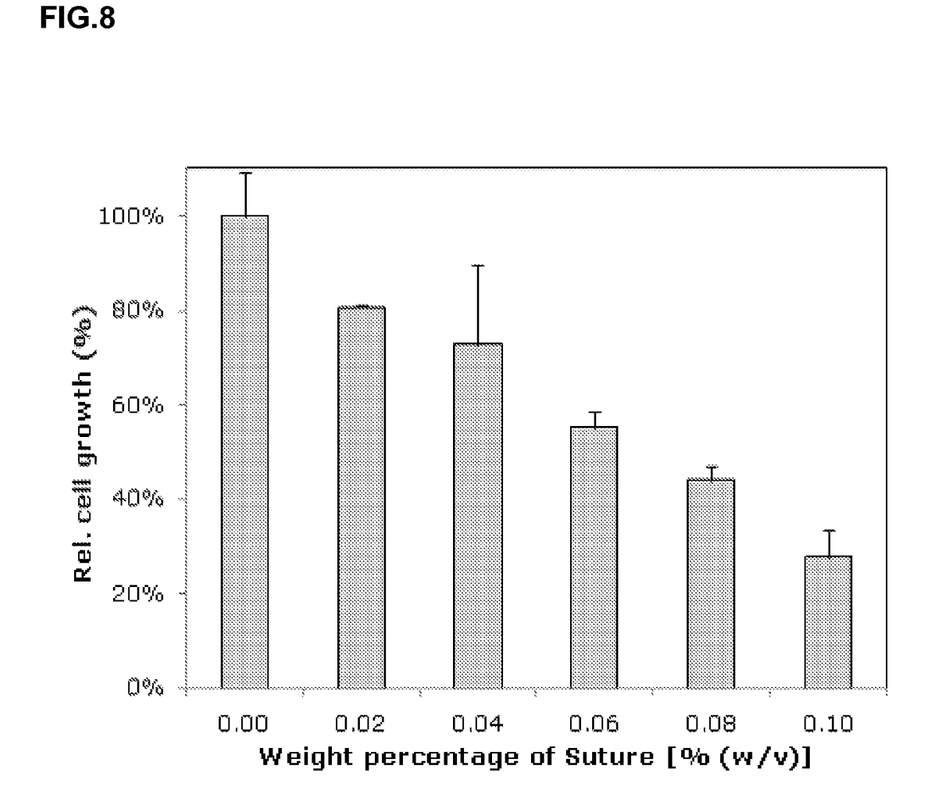
FIG. 8 is a graph and photo that represents the result of the antimicrobial test measuring the antimicrobial activity of the suture that contains the grapefruit extract according to one example of the present invention.

FIG. 8 is a graph showing the comparison of the antimicrobial activity of the strain solution reacting with each of the sutures containing grapefruit seed extracts in various weight percentages. From this, it can be concluded that the growth of the strain is inhibited by the grapefruit seed extract contained in the suture immersed in the cell culture medium and that the higher the amount of suture, the higher the antimicrobial activity.

In particular, it was found that the antimicrobial activity was observed even in a small amount of suture, such as 0.02% (w/v), from which it can be concluded that the antimicrobial activity of the grapefruit seed extract is high, and the antimicrobial activity was observed more than 99% in the suture of 1% (w/v).

As described above, the antimicrobial suture for medical use of the present invention contains the grapefruit extract having an antimicrobial effect to have an antimicrobial function, thus preventing the occurrence of pathogen infection. That is, the antimicrobial suture for medical use of the present invention can improve sanitation, prevent the generation of fungi on the surface thereof, which causes secondary infections during surgery, and stably maintain its strength and tension.

While the invention has been shown and described with reference to certain preferred embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

What is claimed is:

1. A method of manufacturing a medical antimicrobial suture comprising a methanolic grapefruit seed extract containing naringin, ascorbic acid and/or citral, the method comprising:

immersing a biodegradable monofilament suture within a solution comprising an effective amount of the grapefruit seed extract for more than 360 minutes, wherein the grapefruit seed extract is capable of being continuously released in a subject's body for about 70 hours after the antimicrobial suture is inserted into the subject's body.

* * * * *